United States Patent
Bëβmann et al.

(10) Patent No.: US 7,485,853 B2
(45) Date of Patent: Feb. 3, 2009

(54) MASS SPECTROMETRIC MIXTURE ANALYSIS

(75) Inventors: Carsten Bëβmann, Bremen (DE);
Markus Lubeck, Bremen (DE);
Christian Gebhardt, Bremen (DE);
Thorsten Ledertheil, Delmenhorst (DE)

(73) Assignee: Bruker Daltonik GmbH, Bremen (DE)

( * ) Notice: Subject to any disclaimer, the term of this patent is extended or adjusted under 35 U.S.C. 154(b) by 420 days.

(21) Appl. No.: 11/442,655

(22) Filed: May 26, 2006

(65) Prior Publication Data

US 2006/0289737 A1    Dec. 28, 2006

(30) Foreign Application Priority Data

Jun. 3, 2005    (DE) ................ 10 2005 025 499

(51) Int. Cl.
*B01D 59/44* (2006.01)
(52) U.S. Cl. ...................... 250/282; 250/281
(58) Field of Classification Search ................ 250/281, 250/282
See application file for complete search history.

(56) References Cited

U.S. PATENT DOCUMENTS

| | | | |
|---|---|---|---|
| 5,821,534 A * | 10/1998 | Park ........................... | 250/287 |
| 5,970,804 A * | 10/1999 | Robbat, Jr. ................ | 73/863.12 |
| 6,828,550 B2 * | 12/2004 | Griffey et al. ............... | 250/281 |
| 2004/0007666 A1 * | 1/2004 | Griffey et al. ............... | 250/282 |
| 2004/0245452 A1 * | 12/2004 | Bateman et al. ............ | 250/287 |
| 2005/0252275 A1 * | 11/2005 | Kita et al. ................... | 73/23.34 |
| 2005/0288872 A1 * | 12/2005 | Old et al. ..................... | 702/30 |
| 2007/0029477 A1 * | 2/2007 | Miller et al. ................ | 250/290 |
| 2007/0278397 A1 * | 12/2007 | Bateman et al. ............ | 250/286 |

FOREIGN PATENT DOCUMENTS

GB        2 389 704 A        12/2003

* cited by examiner

*Primary Examiner*—Jack I Berman
*Assistant Examiner*—Michael J Logie
(74) *Attorney, Agent, or Firm*—Law Offices of Paul E. Kudirka

(57) ABSTRACT

The invention relates to a mass spectrometric mixture analysis to determine both simple mass spectra of the substances as well as more detailed information about structures and other characteristics of the substances. The invention consists in temporally separating the substance mixture in a separating device, splitting the eluating flow of substances into at least two partial flows and measuring the substances in the different partial flows by mass spectrometry. A direct measurement provides a series of spectra whose evaluation is used for optimal control of the time at which a spectrum of another, delayed partial flow is acquired and the type of this measurement procedure. The substances of the delayed partial flows or their ions can thereby be chemically or physically modified in a variety of ways in order to provide the molecular weight as well as more detailed information.

10 Claims, 1 Drawing Sheet

MASS SPECTROMETRIC MIXTURE ANALYSIS

FIELD OF THE INVENTION

The invention relates to a mass spectrometric mixture analysis to determine both simple mass spectra of the substances as well as more detailed information about structures and other characteristics of the substances.

BACKGROUND OF THE INVENTION

Nowadays mass spectrometric analysis of mixtures, particularly of mixtures of macromolecular substances, for example large biomolecules, generally uses separation methods in liquid phase and ionization of the substances, which are at least partially separated in this way, by electrospray ionization in order to generate the analyte ions. Electrospray ionization is an extremely soft ionization, however, which essentially provides only molecular ions without fragment ions, and hence only results in a determination of the molecular weight of the substances. To be more precise, pseudo-molecular ions are formed. These are protonated or deprotonated ions which differ from the true molecular ions by the weights of the excess or missing protons. Alternative ionization methods such as laser ionization also produce ions which form ions from neutral substances by the addition or removal of protons. In the following, the spectra of pseudo-molecular ions will simply be called "molecular spectra", and "molecular ions" will always be used to describe the pseudo-molecular ions created by adding or removing electrically charged units (protons, and in some cases also alkali ions).

For the best possible characterization and identification of the substances, however, further knowledge is required in addition to the molecular weight, especially information concerning the structure; for proteins, this means information concerning partial sequences of the amino acids. The partial sequences can be determined from spectra of molecular ions which have been fragmented by a suitable method. Other characteristic properties of the substances are obtained by acquiring mass spectra, where the substances or their molecular ions have been chemically or physically modified.

Automated methods for measuring the spectra of fragment ions are usually used to gain information about the structure. Measurement of the fragment ions requires special "tandem mass spectrometers" (often abbreviated to MS/MS), in which fragmentation of suitable, preferably multiply charged, molecular ions is possible; the ions have to be selected beforehand by a mass spectrometric filter. Spectra of this type are frequently called daughter ion spectra; in some mass spectrometers it is possible to select, fragment and measure daughter ions again. One then obtains granddaughter ion spectra. A variety of methods for fragmenting the substances have been elucidated, including fragmentation using high-energy collisions with neutral particles (collision gas), fragmentation by absorption of energy from incident photons, usually in the infrared (IRMPD=infrared multi photon dissociation), and fragmentation resulting from reactions with electrons, negative ions or highly excited neutral particles.

Certain substances can also form ions of a type other than fragment ions if their ions react with other particle. Thus, complex formations with alkali ions, with metal ions or with molecules of solvents (salvation) are sometimes characteristic of certain types of compounds. Their spectra can also be acquired alternately to molecular ions. For example, a method has been published whereby lithium salts are added in the spray capillary to generate lithium ion complexes of substances which are normally difficult to ionize in electrospray ion sources. Reactions of mixtures of multiply positively charged biomolecules with negative ions make it possible to utilize a process called "charge stripping" to produce mixtures of singly charged ions, which are much easier to interpret. The spectra of such ions which are generated in a chemical or physical reaction are grouped together below as "special mass spectra".

In the automatic MS/MS methods mentioned, spectra of molecular ions and fragment ions are acquired in turn. This requires information concerning the occurrence of newly appearing substances, and this information has to be obtained immediately and very rapidly from the molecular spectra just measured. The alternate acquisition of molecular spectra and fragment spectra and the lack of information concerning the concentrations of newly occurring substances to be expected in the future make it impossible to optimize this method, since a decision must be made immediately, using the molecular spectra, as to which molecular ions are to be selected and fragmented. If, despite the temporal separation, the flow of substances contains several overlapping substances (which is practically always the case in complex mixtures), then the decision on a substance can be very difficult because, at best, information about the beginning of a substance batch is available, but there is no complete profile of the substance batch with position and height of the maximum. The substance batches from the separating device (often called "substance peaks") can certainly have a very different concentration and demonstrate complex overlapping patterns. Despite using intelligent algorithms, substances disappear from the substance flow before the spectra of the fragment ions can be scanned. On the other hand, such fragment ion spectra are frequently taken too early, far before the substance has reached its maximum concentration; their quality is then frequently too poor for further processing. There is usually not enough time for a repeat scan, because new substance batches are already appearing.

Depending on the concentration of the substances supplied, scanning the molecular spectra takes only a few tenths of a second in modern mass spectrometers; scanning daughter ion spectra usually takes several times as long. Nevertheless, it is possible to scan between one and five pairs of molecular ion and daughter ion spectra per second.

Conventional liquid chromatography provides substance batches whose profiles can quite easily have a width of roughly between five and thirty seconds. A conventional, automatic scan of daughter ion spectra is quite promising here. However, modern separation methods have ever larger separation selectivities and, associated with this, ever shorter temporal widths of the substance batches separated. The use of very fine capillaries in the so-called nano-LC already shortens the time in which a substance is delivered to a few seconds. In capillary electrophoresis, it is possible to achieve profile widths of the substance batches of between one and three seconds. In electrophoretically mediated capillary chromatography the batch widths are already less than one second. Chip-based micro-separation systems generate substance batch widths of only a few tenths of a second. For separation systems in which the substance mixtures already change rapidly within tenths of a second, an alternate measurement of molecular spectra and daughter ion spectra can no longer be used because of the concentration changes in the time shift between the two measurements, even if the concentration is very high in the substance batches themselves, which makes it possible to have a very short scanning time for the mass spectra.

SUMMARY OF THE INVENTION

The invention consists in temporally separating the substance mixture in a separating device such as a liquid chromatograph, splitting the flow of the substances, which is largely but usually not completely separated, delaying at least one partial flow, and measuring each of the partial flows as series of mass spectra. The direct, non-delayed measurement provides spectral series whose evaluation is used for optimal control of the time at which a spectrum is measured, the progression of the measurement and the type of measurement of the partial flows which are to be measured with delay. The directly measured spectral series of the molecular ions provide prior information on the profiles of the substance batches; this prior knowledge can be used to optimize the measurement of fragment ions of the substances or the measurement of other special mass spectra, also making it possible to especially take into account competing situations of different substances with overlapping profiles, particularly those with very different concentrations.

The delay can quite easily amount to many seconds; where possible, it should be greater than half the profile width of the substance batches, better still greater than the total profile width, in order to obtain a good overview of the development of the concentrations of the individual substances in advance (viewed from the time the delayed substances are measured). Shorter delay times can also profitably be used to control the progression of the measurement, since then at least the build-up behavior of a substance is known.

The substances of the delayed partial flows or their ions can preferably be chemically or physically modified in a variety of ways, for example by fragmentation, to provide not only the molecular weight but also more detailed information as to structures, sequences, affinities, reactivity or other characteristic data of the substances.

The splitting of the substance flows and the delay of at least one partial flow can occur before the ionization, for example be means of a capillary splitter and a delay loop in one of the capillaries leading to the ion sources of which two at least are then present. The splitting can also occur after the ionization, however, by splitting the ion current, in which case the time delay can be achieved by an arrangement of ion storage devices.

The measurement of the spectral series for the partial flows can be conducted in separate mass spectrometers, or in a single mass analyzer by alternating the scanning in a regular or irregular way.

DETAILED DESCRIPTION

Figure 1:
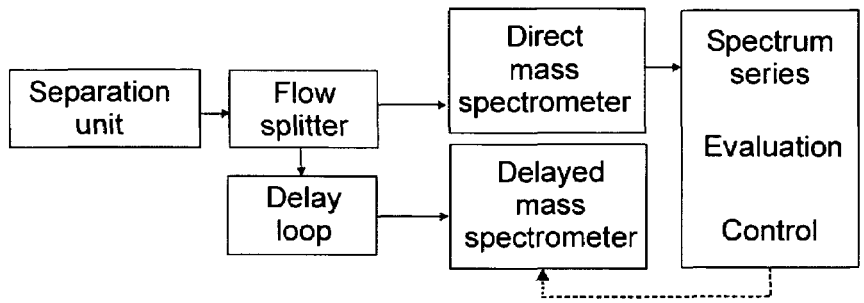
FIG. 1 illustrates the use of two independent mass spectrometers, operated in parallel, the substance flow from the separating device being fed in separately. One part is fed to the second mass spectrometer with a time delay brought about by a capillary loop so that there is enough time to determine the best conditions for the special measurements of the second mass spectrometer from the mass spectra of the directly measured substance flow of the first mass spectrometer, and to control this second mass spectrometer accordingly.

A simple but very effective embodiment using two mass spectrometers operating independently of each other is reproduced in FIG. 1. The substance flow from the separating device, for example a liquid chromatograph, wherein the substances are largely, but in the case of complex substance mixtures by no means completely, separated in time, is split in a capillary splitter. One partial flow is fed without additional delay to the electrospray ion source of the direct mass spectrometer, where it is measured as a series of molecular ion spectra. The direct mass spectrometer used can be a time-of-flight mass spectrometer with orthogonal ion injection, which provides very good mass determinations and a high dynamic range of measurement and enables a rapid sequence of molecular ion spectra to be scanned. These measurements are evaluated in a data system and provide information about the profiles of the substance batches, and above all information about precise molecular masses and their various charge states, before daughter ion spectrum or other special measurements are conducted on the second partial flow. The electrospray ion source not only supplies singly protonated molecular ions but also multiply charged ions, the latter being particularly good for fragmentation.

The profiles of the substance batches from the liquid chromatograph are usually around ten seconds wide. It is then favorable to delay the partial substance flow for the second mass spectrometer by at least five seconds, or better by around 15 seconds. The substance profiles which reach the second mass spectrometer are then known some 15 seconds in advance. This knowledge can be used to determine the most favorable times in each case for acquiring daughter ion spectra for the overlapping substance batches. All information about the masses of the molecular ions and about the relative frequencies of the multiply charged molecular ions, as well as about the characteristic of the concentrations, particularly about the time of the concentration maximum, is available.

The second mass spectrometer can be an RF quadrupole ion trap, for example. This ion trap mass spectrometer makes it relatively simple not only to measure daughter ion spectra but also granddaughter ion spectra, should this type of measurement be advantageous. A disadvantage of the ion trap mass spectrometer is its relatively low dynamic range of measurement, of only some two to three orders of magnitude, to identify substances at very low concentration. This disadvantage can be largely eliminated, however, if the molecular mass of a substance sought is known. The ion trap can then be filled blind with ions of the substance sought, using methods which have been elucidated in principle, and these ions can be isolated and fragmented in a way which has similarly been elucidated. The time-of-flight mass spectrometer operated in parallel now has an extremely high dynamic range of measurement of five to six orders of magnitude. It is therefore also possible to find substances of low concentration and determine their masses with precision. With this information it is then possible to also acquire daughter ion spectra of these substances in the ion trap mass spectrometer. A combination of this type therefore offers particular advantages: precise mass determination of the molecular masses in the time-of-flight mass spectrometer, detection of substances of low concentration in the time-of-flight mass spectrometer, and measurement of the daughter ion spectra to elucidate the structure and unambiguously identify the substance in the ion trap mass spectrometer.

Both mass spectrometers can be operated from a single computer. The spectral series are also stored and evaluated in this computer. It is then particularly simple to undertake feedback control of the second mass spectrometer using the spectral series of the first mass spectrometer. It is not, however, imperative to use only one computer for this task; networked computers are equally suitable. It is favorable and more user-friendly, however, to have the user interface for both mass spectrometers together on one computer.

Figure 2:
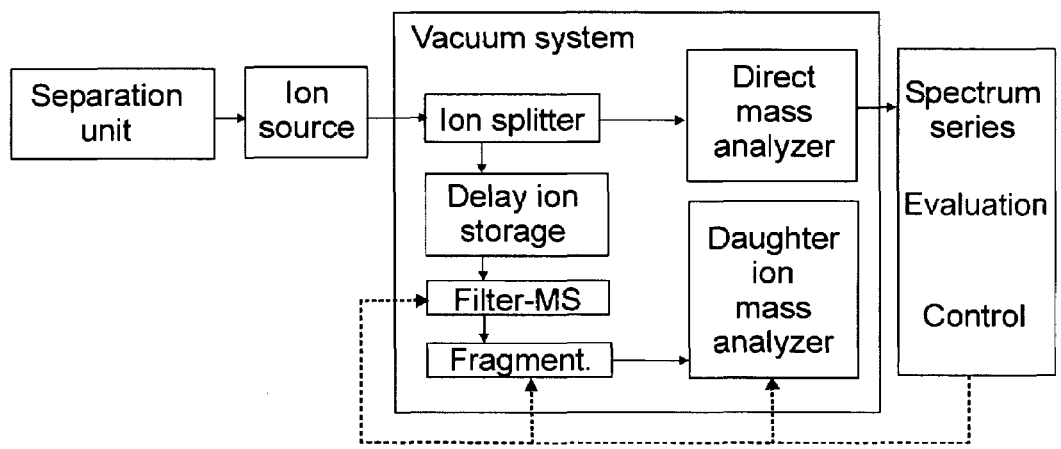
FIG. 2 represents a configuration in which the ion current of the substances is split in the vacuum system. The mass spectra of the ion currents measured directly in the first mass analyzer are used to determine the best conditions for the daughter ion spectra measured in the second mass analyzer with a delay brought about by ion storage devices.

FIG. 2 illustrates an embodiment in which two different mass analyzers are fed by a single ion source, the splitting being produced by an ion current splitter in the vacuum system. A partial ion current is fed to the direct mass analyzer and produces the series of molecular ion spectra whose evaluation is used to optimize the daughter ion spectra acquisition from the daughter ion mass analyzer. The delay is created here by an ion storage devices. In order that the ion currents do not mix temporally, as would be the case in a single ion storage device, a series of ion storage devices designed on the bucket brigade principle can be used. Optimally, each ion storage device of the bucket brigade ion storage device accommodates roughly as many ions as are required for a good daughter ion spectrum. It is possible, for example, to use two identical mass analyzers here, since the parent ions are selected and fragmented outside the second mass analyzer. Both mass analyzers can again be time-of-flight mass spectrometers with orthogonal ion injection, for example. It is also possible, of course, to use an ion trap as the second mass analyzer, in which case the filter mass spectrometer and fragmentation device of FIG. 2 are no longer required, since the selection and fragmentation processes can be carried out in the ion trap mass analyzer itself.

Figure 3:
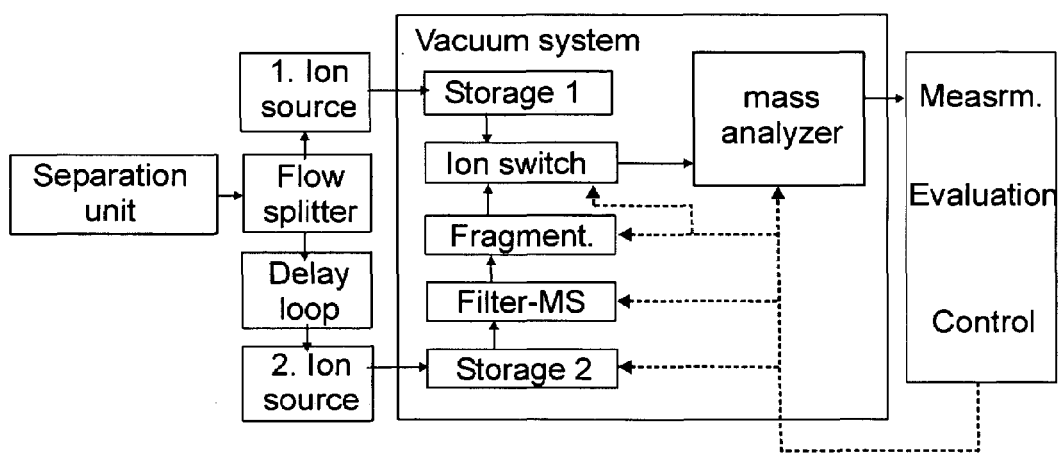
FIG. 3 represents an arrangement in which the two substance flows are measured in different ways in the same mass analyzer, where the directly measured mass spectra are again used to determine optimal conditions for the daughter ion spectra which are to be measured with a time delay.

The arrangement in FIG. 3 is particularly economical because it uses only a single mass analyzer. The split substance flow is fed to two separate ion sources (ion source 1 and ion source 2), once directly, and once delayed in a capillary loop. A capillary loop here should always be basically understood as a lengthening or thickening of a capillary so that the partial flow is delayed; it does not literally have to be a loop. The ions of both ion sources can be temporarily stored in two storage devices (storage device 1 and storage device 2), so that no ions are lost to the measurements. An ion switch allows ions taking the direct path and those taking the delayed path to reach the mass analyzer alternately. The ions on the direct path produce the spectral series which are used to control the measurement of the ions on the delayed path. The alternation of the measurements on the two paths here does not have to be regular. If it seems favorable, after evaluating the directly measured spectral series, it is also possible to conduct several delayed measurements (or direct measurements) one after the other, before switching to the other path.

A particularly favorable mass analyzer here is the analyzer of a time-of-flight mass spectrometer with orthogonal ion injection, since this analyzer enables a high measuring frequency for mass spectra, provides a high mass accuracy, has a high dynamic range of measurement and requires no charge control, but has a stable mass calibration which is independent of the ion current.

A quadrupole filter, as is conventionally used in tandem mass spectrometers, lends itself as the filter mass spectrometer to select the parent ions which are to be subsequently fragmented to daughter ions. Other types of mass filter can also be used, of course, for example a Wien filter. The quadrupole mass filter has the advantage that it can be electrically adjusted for the passage of all ions (above a cut-off limit). This enables a molecular spectrum of the delayed substance flow to occasionally be scanned, if the downstream fragmentation cell is also switched off. A molecular spectrum of this type can be used to monitor the time delay, particularly if a molecular spectrum is scanned when an outgoing and an incoming substance batch overlap. The time delay can shift if the splitting ratio changes, something which could be produced by interferences to the liquid flow in one of the electrospray ion sources.

Possible fragmentation devices particularly include collision cells for collision induced fragmentation (CID), as are used in the majority of tandem mass spectrometers, and also devices for fragmentation using photons, electrons, negative ions or highly-excited neutral particles. Reactions of multiply charged positive ions with slow electrons (ECD=electron capture dissociation), specific negative ions (ETD=electron transfer dissociation) or highly excited atoms provide fragment ions of a type which is different to those from collision induced fragmentation and which provides additional information. Those skilled in the art are aware of how fragmentation cells operate and it therefore does not need to be described in detail here.

The splitter does not necessarily have to divide the substance flow in the ratio of 1:1; it can also produce other splitting ratios if this is more favorable for the delayed daughter ion measurements or special measurements. In a particular embodiment the splitting ratio can be controllable, but this immediately also results in a change to the delay time. A check for measuring the delay time by scanning a molecular spectrum of the delayed ion current is described above. The splitter can also generate more than two partial flows if this is favorable. For example, three partial flows can be generated with two different delays for a basically parallel scanning of molecular ions, daughter ions and granddaughter ions, where knowledge of the substance profiles from the molecular spectra can be used to acquire the daughter ion spectra, and knowledge of the daughter ion spectra can be used to acquire the granddaughter ion spectra. The three partial flows can be measured in three, two or even only one single mass analyzer. Three partial flows can equally be used to acquire daughter ion spectra by CID (collision induced dissociation) and by ECD (electron capture dissociation) or other types of fragmentation in parallel to molecular spectra.

The arrangements introduced in FIGS. 1 to 3 are therefore only examples. With knowledge of this invention, it is quite possible for specialists in this field to construct a very wide range of equipment for methods which are very different, but in all of which mass spectra of substance flows measured in a particular way are controlled by evaluating spectral series which have been measured in advance by means of non-delayed partial flows. The mass spectra scanned in a particular way can be daughter ion spectra, granddaughter ion spectra, and also mass spectra of substances which are otherwise chemically or physically modified or ions. These modifications can be made to the substances in the partial flows of the substances upstream of the ion source, but also to the ions of the substances in the mass spectrometer.

What is claimed is:

1. Method for mass spectrometrically analyzing substance mixtures, comprising the steps of:
   (a) temporally separating the substances of the mixture in a separating device, (b) splitting the flow of temporally separated substances into at least two partial flows, (c) measuring directly a partial flow by a mass spectrometer to obtain a series of mass spectra, and (d) measuring at least one further partial flow mass spectrometrically with a delay in time, the delayed measurements being controlled by an evaluation of the series of mass spectra which are measured directly.

2. Method according to claim 1, wherein the delayed measurements are conducted on ions which have been modified by chemical or physical reactions of the basic substances or of their ions.

3. Method according to claim 2, wherein the delayed measurements are conducted on fragmented ions, whereby daughter ion spectra or granddaughter ion spectra are acquired.

4. Method according to claim 1, wherein the separating device operates with chromatography or electrophoresis or with a combination of both.

5. Method according to claim 1, wherein the splitting of the substance flow is done before the ionization of the substances, and the delay occurs in a capillary delay loop.

6. Method according to claim 1, wherein the splitting of the substance flow occurs after the ionization of the substances as a splitting of the ion currents, and the delay is produced by passing through at least one ion storage device.

7. Method according to claim 6, wherein more than one ion storage device is used in the form of a bucket brigade ion storage devices.

8. Method according to claim 1, wherein the temporal delay corresponds to roughly at least half of the profile width of a substance batch from the separating device.

9. Method according to claim 1, wherein the direct and the delayed measurements are conducted in different mass analyzers.

10. Method according to claim 1, wherein the direct and the delayed measurements are conducted in regular or irregular alternation in the same mass analyzer.

* * * * *